United States Patent [19]

Glass

[11] Patent Number: 5,902,237

[45] Date of Patent: May 11, 1999

[54] METHOD OF OPERATING ACOUSTIC IMAGING

[75] Inventor: Gary Glass, Cambridge, Mass.

[73] Assignee: Hood Laboratories, Pembroke, Mass.

[21] Appl. No.: 09/178,874

[22] Filed: Oct. 26, 1998

[51] Int. Cl.⁶ ...................................................... A61B 5/00
[52] U.S. Cl. ............................................................ 600/407
[58] Field of Search ..................................... 600/529, 533, 600/407; 73/574, 589, 597; 128/898, 899

[56] References Cited

U.S. PATENT DOCUMENTS

| 4,326,416 | 4/1982 | Fredberg | 73/597 |
| 4,909,064 | 3/1990 | Talmadge | 73/4 R |
| 5,445,144 | 8/1995 | Wodicka et al. | 128/207.14 |
| 5,666,960 | 9/1997 | Fredberg et al. | 128/716 |

*Primary Examiner*—George Manuel
*Assistant Examiner*—Eleni Mantis Mercader
*Attorney, Agent, or Firm*—Kane, Dalsimer, Sullivan, Kurucz, Levy, Eisele and Richard, LLP

[57] ABSTRACT

A method of acoustically imaging a portion of the morphology of a subject which includes the steps of utilizing a burst of pulses for which reflections are recorded prior to analyzing and plotting the data generated thereby.

2 Claims, No Drawings

METHOD OF OPERATING ACOUSTIC IMAGING

FIELD OF THE INVENTION

The present invention relates to a method of performing imaging using an acoustic device and, more particularly, a method of reducing testing variable in such imaging.

BACKGROUND OF THE INVENTION

There presently exists devices which provide for acoustic imaging of conduits or cavities. In particular acoustic imaging of the morphology of respiratory tract (rhinograms or pharyngograms) has become available. In U.S. Pat. No. 4,326,416 (the disclosure of which is incorporated herein by reference) there is disclosed an apparatus and method for conducting acoustic measuring. Basically, this involves the generation of a sound pulse which reflection is sensed by a microphone. The acoustical properties of the cavity being explored is then determined. This patent teaches the use of a single electro-acoustic transducer in imaging, U.S. Pat. No. 5,666,960 (the disclosure of which is incorporated herein by reference) teaches the use of two transducers and associated methodology. While the apparatus and method disclosed in these references have shown to be very satisfactory, as in all things, there is a desire to improve upon it particularly, the manner in which the data is obtained.

Typically, in acoustic measuring the following steps occur: 1) an acoustic pulse is generated and its reflections are recorded; 2) the recorded data is analyzed and converted into area versus distance data; 3) a plotting of the area versus distance data occurs; 4) a plurality of sets of area versus distance data (e.g. 10 sets) are stored on a first in first out basis which is then plotted; and 5) the data sets are used to compute a mean and a standard deviation. In essence, the methodology used is to pulse, record, analyze and convert (plot). The foregoing occurs after the user has determined that the data being acquired is acceptable.

While in many applications the foregoing method has been very satisfactory and provided accurate results, it is desired to increase its speed of operation.

SUMMARY OF THE INVENTION

It is a principal object of the invention to improve upon the method of acoustic imaging set forth in the aforenoted patents.

It is a further object to allow for such improvement to be implemented by existing devices merely by changing their methodology of operation rather than complicated physical changes.

In this regard, the present invention envisions the use of a burst method of acquiring data. Rather than having the imaging device pulse record analyze and plot data (once it initially is found to be of an acceptable nature), the device would quickly pulse and record a desired set. After this is done, then the data is analyzed and plotted. This allows for a very quick data acquisition and minimizes test variables such as, for example, patient movement or extreme ambient noise.

DETAILED DESCRIPTION OF THE PREFERRED EMBODIMENT

In the aforementioned patents there is discussed the manner in which the acoustic measuring device is calibrated and the desired data obtained. Initially, the user of the device determines whether good data is being received. The operator can view the signals on a visual display to see if consistent signals representative of the desired image is being received. As noted, slight inopportune movement on the part of the operator or patient can generate faulty data. However, once consistent data is obtained, the acoustic waves or propergated, reflected, sensed and processed. That being the acoustic pulse is launched, data recorded (area versus distance), analyzed (ten sets of data are kept FIFO) and plotted, and when acquisition is stopped, mean and standard deviation are computed.

While such methodology has worked fine in the past, an improved methodology is as follows. Data is acquired as above to determine if the data being received is good (i.e. for example to see if the acoustic device should be repositioned etc.) Each pulse is launched, recorded, analyzed and plotted with the data for the last ten pulses saved in a FIFO buffer.

The user then, via a display of the data, determines whether it is acceptable. Each set typically takes 2–5 seconds to be generated, recorded, analyzed and plotted. If it is acceptable, then the user launches a series of pulses (e.g. ten or more depending upon the desired set amount). The pulses can also be automatically generated by equipment monitoring the subject. These pulses are rapidly launched and then respective reflections recorded. only then is the pulse data analyzed, plotted and averaged.

The aforesaid method allows the user to position the acoustic device or subject (which may be, in addition to humans, a horse or other animal in some instances) and take a set of pulses rapidly with no time spent between pulses for analyzing or plotting data. This quick method can capture fast events forced by a subject moving (posture change) triggered from an event such as breathing or a particular flow rate or lung volume, or testing conditions which require rapid acquisition, such as extreme ambient noise.

Thus by the present invention its objects and advantages are realized and, although a preferred embodiment has been disclosed and described in detail herein, its scope should note be limited thereby rather its scope should be determined by that of the appended claims.

What is claimed is:

1. A method for acoustically imaging a portion of the internal morphology of a mammal including humans, which includes the steps of:

a) generating an acoustic pulse;

b) recording the reflection;

c) analyze the recorded data and converting it to area versus distance data;

d) plotting the area versus distance data;

e) generating a set of area versus distance data stored on a first in, first out basis which sets are plotted and a mean and standard deviation determined:

the improvements comprising the following steps:

f) performing one or more of the steps a–e above to determine if the data being received is accurate;

g) if accurate, performing step a and b above in bursts of sets before performance of any of the subsequent steps c–e.

2. The method in accordance with claim 1 wherein the bursts involve generating approximately 10 pulses or more successively at a time which are recorded.

* * * * *